(12) United States Patent
Bawendi et al.

(10) Patent No.: US 6,617,583 B1
(45) Date of Patent: Sep. 9, 2003

(54) INVENTORY CONTROL

(75) Inventors: Moungi G. Bawendi, Boston; Klavs F. Jensen, Lincoln, both of MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/160,458

(22) Filed: Sep. 24, 1998

Related U.S. Application Data (60) Provisional application No. 60/101,046, filed on Sep. 18, 1998.

(51) Int. Cl.⁷ .............................. G01J 1/24; G06K 7/10; C22C 18/00; C22C 18/04

(52) U.S. Cl. ............................ 250/370.01; 235/462.01; 435/DIG. 31; 435/DIG. 33; 420/513; 420/525; 420/528; 420/555; 420/556; 420/903

(58) Field of Search ................................ 423/299, 289, 423/290; 420/528, 555, 576, 577, 513, 525, 556, 903; 235/462, 472, 454, 456, 487, 494, 462.01; 435/6, 91.2, 91.1, 7.1, 4, 8, 68.1, 23, 24, DIG. 33, 33; 436/501, 518, 524, 531, 528, 86, 89, 90, 94; 530/300, 307.1, 333, 335, 334; 250/370.01

(56) References Cited

U.S. PATENT DOCUMENTS

| | | | |
|---|---|---|---|
| 3,996,345 A | 12/1976 | Ullman et al. ................ 424/12 |
| 4,637,988 A | 1/1987 | Hinshaw et al. ............. 436/546 |
| 4,777,128 A | 10/1988 | Lippa ............................ 435/5 |
| 5,262,357 A | 11/1993 | Alivisatos et al. .......... 437/233 |
| 5,293,050 A | 3/1994 | Chapple-Sokol et al. ..... 257/17 |
| 5,304,786 A | 4/1994 | Pavlidis et al. ............. 235/462 |
| 5,354,707 A | 10/1994 | Chapple-Sokol et al. ... 437/106 |
| 5,395,791 A | 3/1995 | Cheng et al. ................ 437/105 |
| 5,422,489 A | 6/1995 | Bhargava ................. 250/488.1 |
| 5,492,080 A | 2/1996 | Ohkawa et al. ............. 117/108 |
| 5,499,260 A | 3/1996 | Takahashi et al. ............ 372/46 |
| 5,505,928 A | 4/1996 | Alivisatos et al. .......... 423/299 |
| 5,515,393 A | 5/1996 | Okuyama et al. ............. 372/45 |
| 5,525,377 A | 6/1996 | Gallagher et al. .......... 427/512 |
| 5,537,000 A | 7/1996 | Alivisatos et al. .......... 313/506 |
| 5,541,948 A | 7/1996 | Krupke et al. ................ 372/41 |
| 5,565,324 A | 10/1996 | Still et al. |
| 5,585,640 A | 12/1996 | Huston et al. ........... 250/483.1 |
| 5,625,456 A | 4/1997 | Lawandy .................... 356/376 |
| 5,674,698 A | 10/1997 | Zarling et al. ............. 435/7.92 |
| 5,721,099 A | 2/1998 | Still et al. |
| 5,736,330 A | 4/1998 | Fulton ............................ 435/6 |
| 5,747,180 A | 5/1998 | Miller et al. .................. 372/41 |
| 5,751,018 A | 5/1998 | Alivisatos et al. ............ 257/64 |
| 5,770,299 A | 6/1998 | Dannenhauer et al. ...... 428/195 |
| 5,789,162 A | 8/1998 | Dower et al. .................. 435/6 |
| 5,985,353 A | 11/1999 | Lawton et al. ............. 427/2.13 |
| 5,990,479 A | * 11/1999 | Weiss et al. ................ 250/307 |
| 6,355,432 B1 | 3/2002 | Fodor et al. ................... 435/6 |

FOREIGN PATENT DOCUMENTS

| | | |
|---|---|---|
| WO | 95/29473 | 11/1995 |
| WO | WO 98/04740 | 2/1998 |
| WO | WO 98/19963 | 5/1998 |
| WO | WO 98/33070 | 7/1998 |
| WO | WO 98/36376 | 8/1998 |
| WO | WO 98/46372 | 10/1998 |

OTHER PUBLICATIONS

Alivisatos et al., "Semiconductor Clusters, Nanocrystals, and Quantum Dots," *Science*, 271:933–937, 1996.

Bawendi et al., "Luminescence properties of CdSe quantum crystallites: resonance between interior and surface localized states," *J. Chem. Phys.*, 96(2):946–954, 1992.

Beverloo et al., "Preparation and Microscopic Visualization of Multicolor Luminescent Immunophosphors," *Cytometry*, 13:561–570, 1992.

Colvin et al., "Light–emitting diodes made from cadmium selenide nanocrystals and a semiconducting polymer" *Nature*, 370(6488) 354–357, Aug. 4, 1994.

Cook, "Scintillation Proximity Assay: A Versatile High–Throughput Screening Technology," *Drug Discovery Today*, 1:287–294, 1997.

Correa–Duarte et al., "Stabilization of CdS semiconductor nanoparticles against photodegradation by silica coating procedure," *Chem. Phys. Lett.*, 286:497–501, 1998.

(List continued on next page.)

*Primary Examiner*—Jyothsna Venkat
*Assistant Examiner*—Tomm Friend
(74) *Attorney, Agent, or Firm*—Fish & Richardson P.C.

(57) ABSTRACT

A novel encoding system and methods for determining the location and/or identity of a particular item or component of interest is provided. In particular, the present invention utilizes a "barcode" comprising one or more sizes of semiconductor nanocrystals (quantum dots) having characteristic spectral emissions, to either "track" the location of a particular item of interest or to identify a particular item of interest. The semiconductor nanocrystals used in the inventive "barcoding" scheme can be tuned to a desired wavelength to produce a characteristic spectral emission in narrow spectral widths, and with a symmetric, nearly Gaussian line shape, by changing the composition and size of the quantum dot. Additionally, the intensity of the emission at a particular characteristic wavelength can also be varied, thus enabling the use of binary or higher order encoding schemes. The information encoded by the quantum dot can be spectroscopically decoded, thus providing the location and/or identity of the particular item or component of interest. In particular, a single primary light source can be used to decode the inventive barcode. In particularly preferred embodiments, the present system and method is used in applications to security systems, to the tracking of consumer items such as jewelry, vehicles, or paper. In other particularly preferred embodiments, the present system and method is used in applications for biochemistry to track the location of biomolecules such as DNA sequences, combinatorial chemistry, and genomics for encoding and probe identifiers.

21 Claims, 5 Drawing Sheets

(1 of 5 Drawing Sheet(s) Filed in Color)

OTHER PUBLICATIONS

Dabbousi et al., "Electroluminescence from CdSe quantum–dot/polymer composites" *Appl. Phys. Lett.*, 66(11):1316–1318, Mar. 13, 1995.

Fox et al., "Fluorescence and Redox Activity of Probes Anchored through an Aminotrithiol to Polycrystalline Gold" *Langmuir*, 14:816–820, 1998.

Gan et al., "Enhanced Photoluminescence and Characterization of Mn–Doped ZnS Nanocrystallites Synthesized in Microemulsion" *Langmuir*, 1997(13):6427–6431, 1997.

Guha et al., "Hybrid organic–inorganic semiconductor-based light–emitting diodes" *J. Appl. Phys.*, 82(8):4126–4128, Oct. 15, 1997.

Jarvis et al., "Solution Synthesis and Photoluminescence Studies of Small Crystallites of Cadmium Telluride," *Mat. Res. Soc. Symp. Proc.*, 272:229–234, 1992.

Kagan et al., "Electronic Energy Transfer in CdSe Quantum Dot Solids," *Physical Review Letters*, 76:1517–1520, 1996.

Lawless et al., "Bifunctional Capping of CdS Nanoparticles and Bridging to TiO2" *J. Phys. Chem.*, 99:10329–10335, 1995.

Lee et al., "Surface Derivatization of Nanocrystalline CdSe Semiconductors," *Mat. Res. Soc. Symp. Proc.*, 452:323–328, 1997.

Liz–Marzan et al., "Synthesis of Nanosized Gold–Silica Core–Shell Particles" *Langmuir*, 12:4329–4335, 1996.

Mahtab et al., "Protein–sized quantum dot luminescence can distinguish between 'straight', 'bent', and 'kinked' oligonucletides", *J. Am. Chem. Soc.*, 117:9099–9100, 1995.

Mahtab et al., "Preferential–absorption of a 'kinked' DNA to a newtral curved surface: comparison to and implications for nonspecific DNA–protein interactions," *J. Am. Chem. Soc.*, 118:7028–7032, 1996.

Mikulec et al., "Fluorescent Semiconductor Nanocrystallites Derivatized with Biomolecules," 216th *American Chemical Society National Meeting & Exposition Program,* Boston, MA, Aug. 23–27, 1998.

Müllenborn et al., "Characterization of Solution–Synthesized CdTe and HgTe," *Applied Physics,* 56:317–321, 1993.

Murphy et al., "Quantum dots as inorganic DNA–binding proteins," *Mat. Res. Soc. Symp.*, 452:597–600, 1997.

Peng et al., "Epitaxial Growth of Highly Luminescent CdSe/CdS Core/Shell Nanocrystals with Photostability and Electronic Accessibility," *J. Am. Chem. Soc.,* 119:7019–7029, 1997.

Peng et al., "Synthesis and Isolation of a Homodimer of Cadmium Selenide Nanocrystals," *Angewandte Chemie,* 36:145–147, 1997.

Rajh et al., "Synthesis and Characterization of Surface–Modified Colloidal CdTe Quantum Dots" *J. Phys. Chem.,* 97:11999–12003, Nov. 1993.

Rogach et al., "Synthesis and characterization of Thiol–Stabilized CdTe Nanocrystals" *Ber. Bunsenges. Phys. Chem.,* 100(11):1772–2778, 1996.

Schröck et al., "Multicolor Spectral Karyotyping of Human Chromosomes," *Science*, 273:494–497, 1996.

Spanhel et al., "Photochemistry of Colloidal Semiconductors. Surface Modification and Stability of Strong Luminescing CdS Particles" *J. Am. Chem. Soc.,* 109(19):5649–5655, 1987.

Steigerwald et al., "Surface Derivatization and Isolation of Semiconductor Cluster Molecules," *J. Am. Chem. Soc.*, 110:3046–3050, 1988.

Kagan et al., "Long–range resonance transfer of electronic excitations in close–packed CdSe quantum–dot solids" *The American Physical Society*, Physical Review B, vol. 54, No. 12:8633–8643, Sep. 15, 1996–II.

Baldwin et al., "Synthesis of a Small Molecule Combinatorial Library Encoded with Molecular Tags" *J. Am. Chem. Soc.* 117:5588–89, 1995.

Czarnik, Anthony W., "Encoding methods for combinatorial chemistry", *Curr Opin Chem Biol.* 1(1):60–6, 1997.

Plunkett et al., "Combinatorial chemistry and new drugs", *Sci Am.* 276(4):68–73, 1997.

Kortan, et al., "Nucleation and Growth of CdSe on ZnS Quantum Crystallite Seeds, and Vice Versa, in Inverse Micelle Media," *J. Am. Chem. Soc.* 112:1327–1332, 1990.

Coffer, et al., "Characterization of quantum–confined CdS Nanocrystallites stabilized by deoxyribonucleic acid (DNA)," *Nanotechnology* 3:69–76, 1992.

Murray, et al., "Synthesis and Characterization of Nearly Monodisperse CdE (E=S, Se, Te) Semiconductor Nanocrystallites," *J. Am. Chem. Soc.* 115(19):8706–8715, 1993.

Whitesell, et al., "Directionally Aligned Helical Peptides on Surfaces," *Science* 261:73–76, Jul. 1993.

Moran, et al., "Radio Frequency Tag Encoded Combinatorial Library Method for the Discovery of Tripeptide–Substituted Cinnamic Acid Inhibitors of the Protein Tyrosine Phosphatase PTP1B," *J. Am. Chem. Soc.* 117:10787–10788, 1995.

Nicolaou, et al., "Radiofrequency Encoded Combinatorial Chemistry," *Ingew. Chem. Int. Ed. Engl.* 34(20):2289–2291, 1995.

Alivisatos, "Perspectives on the Physical Chemistry of Semiconductor Nanocrystals," *J. Phys. Chem.* 1996(100):13226–13239, 1996.

Danek, et al., "Synthesis of Luminescent Thin–Film CdSe/ZnSe Quantum Dot Composites Using CdSe Quantum Dots Passivated with an Overlayer of ZnSe," *Chem. Mater.* 8(1):173–180, 1996.

Matsumoto, et al., "Preparation of Monodisperse CdS Nanocrystals by Size Selective Photocorrosion," *J. Phys. Chem* 100(32):13781–13785, 1996.

Hines, et al., "Synthesis and Characterization of Strongly Luminescing ZnS–Capped CdSe Nanocrystals," *J. Phys. Chem.* 100:468–471, Jan. 1996.

McGall, et al., "Light–directed synthesis of high–density oligonucleotide arrays using semiconductor photoresists," *Proc. Natl. Acad. Sci. USA* 93:13555–13560, Nov. 1996.

Chee, et al., "Accessing Genetic Information with High–Density DNA Arrays," *Science* 274(5287):610–614, Oct. 25, 1996.

Empedocles, et al., "Photoluminescence Spectroscopy of Single CdSe Nanocrystallite Quantum Dots," *Phys. Rev. Lett.* 77(18):3873–3876, Oct. 1996.

Nirmal, et al., "Fluorescence Intermittency in single Cadmium Selenide Nanocrystals," *Nature* 383:802–804, Oct. 1996.

Egner, et al., "Tagging in combinatorial chemistry: the use of coloured and fluorescent beads," *Chem. Commun.*:735–736, 1997.

Empedocles, et al., "Quantum–Confined Stark Effect in Single CdSe Nanocrystallite Quantum Dots," *Science* 278:2114–2117, Dec. 1997.

Fodor, "Techwire," *Science* 277(5324):393–395, Jul. 18, 1997.

Kuno, et al., "The band edge luminescence of surface modified CdSe nanocrystallites: Probing and luminescing state," *J. Chem. Phys.* 106(23):9869–9882, Jun. 1997.

Dabbousi, et al., "(CdSe)ZnS core–shell quantum dots: synthesis and characterization of a size series of highly luminescent nanocrystallites," *J. of Phys. Chem. B* 101(46):9463–9475, Nov. 13, 1997.

Michael, et al., "Randomly Ordered Addressable High–Density Optical Sensor Arrays," *Analyt. Chem.* 70(7):1242–1248, Apr. 1998.

Winzeler, et al., "Direct Allelic Variation Scanning of the Yeast Genome," *Science* 281:1194–1197, Aug. 1998.

Wang, et al., "Large–Scale Identification, Mapping, and Genotyping of Single–Nucleotide Polymorphisms in the Human Genome," *Science* 280:1077–1082, May 1998.

Mikulec, et al., "Fluorescent semiconductor nanocrystallites derivatized with biomolecules," *Amer. Chem. Soc. Nat'l Meeting*, Boston, MA, Aug. 24, 1998.

Service, "Semiconductor Beacons Light Up Cell Structures," *Science* 281:1930–1931, Sep. 25, 1998.

Jacoby, "Quantum dots meet biomolecules," *C&E News*:8, Sep. 28, 1998.

Bruchez, et al., "Semiconductor Nanocrystals as Fluorescent Biological Labels," *Science* 281:2013–2016, Sep. 1998.

Chan, et al., "Quantum Dot Bioconjugates for Ultrasensitive Nonisotopic Detection," *Science* 281:2016–2018, Sep. 1998.

Wade, "In the Hunt for Useful Genes, a Lot Depends on "Snips"," :C1,C5, Aug. 11, 1998.

Lett, "Color–Coding Quantum Dots Debut With Promising Careers In Clinical Diagnostics Field," :1–2, Sep. 25, 1998.

Alivisatos, "Perspectives on the Physical Chemistry of Semiconductor Nanocrystals," J. Phys. Chem., 100, pp. 13226–13229, 1996.*

Danek et al., "Synthesis of Luminescent Thin–Film CdSe/ZnSe Quantum Dot Composites Using CdSe Quantum Dots Passivated with an Overlayer of ZnSe," Chem. of Materials, 8, pp. 173–180 1996.*

Bawendi et al., "(CdSe)ZnS Core–Shell Quantum Dots: Synthesis and Characterization of a Size Series of Highly Luminescent Nanocrystallites," J. Phys. Chem., 101, 9463–9475, 1997.*

Bawendi et al., Poster Presentation Entitled: "Fluorescent Semiconductor Nanocrystallites Derivatized With Biomolecules," Presented at the 216th National Meeting of the American Chemical Society, Aug. 23–27, 1998.*

\* cited by examiner-

INVENTORY CONTROL

This application Related Applications claims priority to the co-pending provisional application U.S. Patent Application Ser. No. 60/101,046 entitled "Inventory Control" filed on Sep. 18, 1998, which is incorporated in its entirety by reference. This application is related to the following application which was filed in even day herewith and which is incorporated in its entirety by reference: application entitled "Biological Applications of Quantum Dots". Additionally, this application is also related to the following application, which was filed on Sep. 18, 1998, and which is incorporated in its entirety by reference: application entitled "Water Soluble Luminescent Nanocrystals".

A portion of the disclosure of this patent document contains material which is subject to copyright protection. The copyright owner has no objection to the reproduction by anyone of the patent document or the patent disclosure, as it appears in the Patent and Trademark Office patent file or records, but otherwise reserves all copyright rights whatsoever.

This invention was made with government support under Grant Number DMR-9400334 awarded by the National Science Foundation. The United States government may have certain rights in the invention.

BACKGROUND OF THE INVENTION

The ability to track the location or identity of a component or item of interest has presented a significant challenge for industry and science. For example, the demands of keeping track of consumer products, such as items in a grocery store or jewelry, and the interest in identification devices, such as security cards, has led to the need for a secure and convenient system. Additionally, emerging technologies such as combinatorial chemistry, genomics research, and microfluidics also require the ability to identify and track the location of large numbers of items.

A traditionally used method for tracking the location or identity of a component or item of interest is Universal Product Code technology, or barcode technology, which uses a linear array of elements that are either printed directly on an object or on labels that are affixed to the object. These bar code elements typically comprise bars and spaces, with bars of varying widths representing strings of binary ones and spaces of varying widths representing strings of binary zeros. Bar codes can be detectable optically using devices such as scanning laser beams or handheld wands, or they can be implemented in magnetic media. The readers and scanning systems electro-optically decode the symbol to multiple alpha-numerical characters that are intended to be descriptive of the article or some characteristic thereof. Such characters are typically represented in digital form as an input to a data processing system for applications in point-of-sale processing and inventory control to name a few.

Although traditional bar codes typically only contain five or six letters or digits, two dimensional barcodes have also been developed in which one-dimensional bar codes are stacked with horizontal guard bars between them to increase the information density. For example, U.S. Pat. No. 5,304,786 describes the use of a high density two-dimensional bar code symbol for use in bar code applications. Unfortunately, although the information density of barcode technology has improved, this technology is often easily destructible, and the interference of dust, dirt and physical damage limits the accuracy of the information acquired from the readout equipment. Additionally, because of the difficulty of etching the barcode on many items, it is also difficult to apply to a wide range of uses.

Another technology that has been developed for labeling objects includes a composition comprising silicon or silicon dioxide microparticles and a powder, fluid or gas to be applied to objects such as vehicles, credit cards and jewelry (WO 95/29437). This system typically allows the formation of 200 million particles on a single wafer, each of the particles on one wafer being designed to be of identical shape and size so that when the particles are freed from the wafer substrate one is left with a suspension containing a single particle type which can thus be identified and associated with a particular item of interest. This system, although information dense, is also not practical for a wide range of application. One of the advantages explicitly stated in the application includes the unlikely event of unauthorized replication of the particles because of the non-trivial process of micromachining used which requires specialized equipment and skills. Thus, this process would not be widely amenable to a range of uses for inventory control.

In addition to abovementioned barcoding and microparticle inventory control schemes, emerging technologies such as combinatorial chemistry have also resulted in the development of various encoding schemes (See, for example, Czamik, A. W., "Encoding Methods for Combinatorial Chemistry", *Curr. Opin. Chem. Biol.,* 1997, 1, 60). The need for this development has arisen in part from the split and pool technique utilized in combinatorial chemistry to generate libraries on the order of one million compounds. Split and pool synthesis involves dividing a collection in beads into N groups, where N represents the number of different reagents being used in a particular reaction stage, and after the reaction is performed, pooling all of these groups together and repeating the split and pool process until the desired reaction sequence is completed. Clearly, in order to keep track of each of the compounds produced from a reaction series, the beads must be "tagged" or encoded with information at each stage to enable identification of the compound of interest or the reaction pathway producing the compound. The tags used to encode the information, however, must be robust to the conditions being employed in the chemical synthesis and must be easily identifiable to obtain the information. Exemplary encoding techniques that have been developed include the use of chemically robust small organic molecules ("tags") that are cleaved from the bead after the synthesis is completed and analyzed using mass spectroscopy. (U.S. Pat. Nos. 5,565,324; 5,721,099). The disadvantage of this method is that the "tags" must be cleaved from the bead in order to gain information about the identity of the compound of interest.

In response to this, several groups have developed encoding schemes that allow analysis while the "tags" are still attached to the supports. For example, Radiofrequency Encoded Combinatorial (REC™) chemistry combines recent advances in microelectronics, sensors, and chemistry and uses a Single or Multiple Addressable Radiofrequency Tag (SMART™) semiconductor unit to record encoding and other relevant information along the synthetic pathway (Nicolaou et al., *Angew. Chem. Int. Ed. Engl.* 1995, 34, 2289). The disadvantage of this system, however, is that the SMART™ memory devices utilized are very large in size (mm), and thus scanning the bead to decode the information becomes difficult. Another example of on-bead decoding includes the use of colored and fluorescent beads ( Egner et al., *Chem. Commun.* 1997, 735), in which a confocal microscope laser system was used to obtain the fluorescence spectra of fluorescent dyes. The drawback of this method, however, is the tendency of the dyes to undergo internal quenching by either energy transfer or reabsorption of the emitted light. Additionally, this system is not able to uniquely and distinctly identify a range of dyes.

Clearly, it would be desirable to develop a general information dense encoding system flexible, robust and practical enough to be utilized both in general inventory control and in emerging technologies. This system would also be capable of distinctly and uniquely identifying particular items or components of interest.

SUMMARY OF THE INVENTION

The present invention provides a novel encoding system and methods for determining the location and/or identity of a particular item or component of interest. In particular, the present invention utilizes a "barcode" comprising one or more particle size distributions of semiconductor nanocrystals (quantum dots) having characteristic spectral emissions to either "track" the location of a particular item of interest or to identify a particular item of interest. The semiconductor nanocrystals used in the inventive "barcoding" scheme can be tuned to a desired wavelength to produce a characteristic spectral emission by changing the composition and size of the quantum dot. Additionally, the intensity of the emission at a particular characteristic wavelength can also be varied, thus enabling the use of binary or higher order encoding schemes. The information encoded by the quantum dot can be spectroscopically decoded, thus providing the location and/or identity of the particular item or component of interest.

In a particularly preferred embodiment, the method involves providing a composition comprising an item of interest, and one or more sizes of semiconductor nanocrystals having characteristic spectral emissions, or providing a composition comprising a support, an item of interest, and one or more sizes of semiconductor nanocrystals; subjecting said composition to a primary light source to obtain the spectral emissions for said one or more sizes of quantum dots on said composition; and correlating said spectral emission with said item of interest. The present method, in preferred embodiments, can be used to encode the identity of biomolecules, particularly DNA sequences, or other items, including, but not limited to, consumer products, identification tags and fluids.

In another aspect, the present invention provides compositions. In one particularly preferred embodiment, the composition comprises a support, and one or more particle size distributions of semiconductor nanocrystals having different characteristic spectral emissions. In another particularly preferred embodiment, the composition comprises a support, one or more items of interest and one or more sizes of quantum dots having different characteristic spectral emissions. In yet another preferred embodiment, the composition comprises an item of interest and one or more sizes of quantum dots having different characteristic spectral emissions. The quantum dots can be associated with, attached thereto, or embedded within said support structure. Additionally, the quantum dot can optionally have an overcoating comprised of a material having a band gap greater than that of the quantum dot.

In yet another aspect, the present invention provides libraries of compounds and/or items of interest. In a particularly preferred embodiment, each compound in the library is bound to an individual support, and each support has attached thereto or embedded therein one or more identifiers comprising one or more particle size distributions of quantum dots having characteristic spectral emissions. In yet another preferred embodiment, each item of interest has attached thereto, or embedded therein one or more identifiers comprising one or more particle size distributions of quantum dots having characteristic spectral emissions.

In yet another aspect, the present invention also provides kits for identifying an item of interest comprising a collection of items of interest, and wherein each member of said collection of objects has attached thereto or embedded therein one or more particle size distributions of quantum dots having characteristic spectral emissions. In another preferred embodiment, the kit comprises a collection of item is of interest, each bound to a solid support, wherein each support has attached thereto, associated therewith, or embedded therein one or more unique identifiers.

In another aspect, the present invention provides methods for identifying a compound having a particular characteristic of interest comprising providing a library of compounds, testing said library of compounds for a particular characteristic of interest, observing the photoluminescence spectrum for each identifier attached to each support containing a compound of interest, and identifying the compound of interest by determining the reaction sequence as encoded by said one or more sizes of quantum dots. In yet another particularly preferred embodiment, the step of identifying the reaction sequence can be determined before testing the library of compounds because the reaction sequence can be recorded during the synthesis of the compound by "reading" the beads (i.e., observing the photoluminescence spectrum) prior to each reaction step to record the reaction stages. The present invention additionally provides methods for recording the reaction stages of a synthesis concurrently with the synthesis.

In yet another aspect, the present invention provides methods for identifying a molecule having a characteristic of interest comprising contacting a first library of molecules with a second library of molecules, wherein each of the molecules in the first library is encoded using one or more sizes of quantum dots and the second library has attached thereto or embedded therein one or more sizes of quantum dots acting as "probes". This method provides simultaneously a way to identify the binding of one or more molecules from the second library to the first library and determining the structure of said one or more molecules from the first library.

Definitions

"Quantum dot": As used herein, the term "quantum dot" means a semiconductor nanocrystal with size dependent optical and electrical properties. In particular, the band gap energy of a quantum dot varies with the diameter of the crystal.

"Identification unit or barcode": As used herein, the term "identification unit" is used synonymously with the term "barcode", and comprises one or more sizes of quantum dots, each size of quantum dot having a characteristic emission spectrum. The "identification unit" or "barcode" enables the determination of the location or identity of a particular item or matter of interest.

"Item of interest": As used herein, the term "item of interest" is used synonymously with the term "component of interest" and refers to any item, including, but not limited to, consumer item, fluid, gas, solid, chemical compound, and biomolecule.

"Biomolecule": As used herein, the term "biomolecule" refers to molecules (e.g., proteins, amino acids, nucleic acids, nucleotides, carbohydrates, sugars, lipids, etc.) that are found in nature.

"One or more sizes of quantum dots": As used herein, the phrase "one or more sizes of quantum dots" is used synonymously with the phrase "one or more particle size distributions of quantum dots". One of ordinary skill in the art will realize that particular sizes of quantum dots are actually obtained as particle size distributions.

DESCRIPTION OF THE DRAWING

The file of this patent contains at least one drawing executed in color. Copies of this patent with color drawing(s) will be provided by the Patent and Trademark Office upon request and payment of the necessary fee.

DESCRIPTION OF CERTAIN PREFERRED EMBODIMENTS

Recognizing the need to identify and locate specific items or components of interest, the present invention provides a novel encoding system. In particular, the present invention utilizes a "barcode" comprising one or more particle size distributions of semiconductor nanocrystals (quantum dots), having characteristic spectral emissions, to either "track" the location of a particular item of interest or to identify a particular item of interest. The semiconductor nanocrystals used in the inventive "barcoding" scheme can be tuned to a desired wavelength to produce a characteristic spectral emission by changing the composition and size of the quantum dot, and additionally, the intensity of the emission at a particular characteristic wavelength can also be varied, thus enabling the use of binary or higher order encoding schemes. The information encoded by the quantum dots can be spectroscopically decoded, thus providing the location and/or identity of the particular item or component of interest.

The ability of the semiconductor nanocrystals to be utilized in the inventive barcode system results from their unique characteristics. Semiconductor nanocrystals have radii that are smaller than the bulk exciton Bohr radius and constitute a class of materials intermediate between molecular and bulk forms of matter. Quantum confinement of both the electron and hole in all three dimensions leads to an increase in the effective band gap of the material with decreasing crystallite size. Consequently, both the optical absorption and emission of quantum dots shift to the blue (higher energies). Upon exposure to a primary light source, each quantum dot distribution is capable of emitting energy in narrow spectral widths, as narrow as 25–30 nm, and with a symmetric, nearly Gaussian line shape, thus providing an easy way to identify a particular quantum dot. As one of ordinary skill in the art will realize, the linewidths are dependent on the size heterogeneity of the quantum dots in each preparation. Single quantum dot complexes have been observed to have full width half max as narrow as 12–15 nm.

In addition, quantum dot distributions with larger linewidths in the range of 40–60 nm can be readily made and have the same physical characteristics as quantum dots with narrower linewidths.

Exemplary materials for use as quantum dots in the present invention include, but are not limited to group II–VI, III–V and group IV semiconductors such as ZnS, ZnSe, ZnTe, CdS, CdSe, CdTe, GaN, GaP, GaAs; GaSb, InP, InAs, InSb, AlS, AlP, AlSb, PbS, PbSe, Ge and Si and ternary and quaternary mixtures thereof. The semiconductor nanocrystals are characterized by their uniform nanometer size. By "nanometer" size, it is meant less than about 150 Angstroms (Å), and preferably in the range of 12–150 Å.

Figure 1:
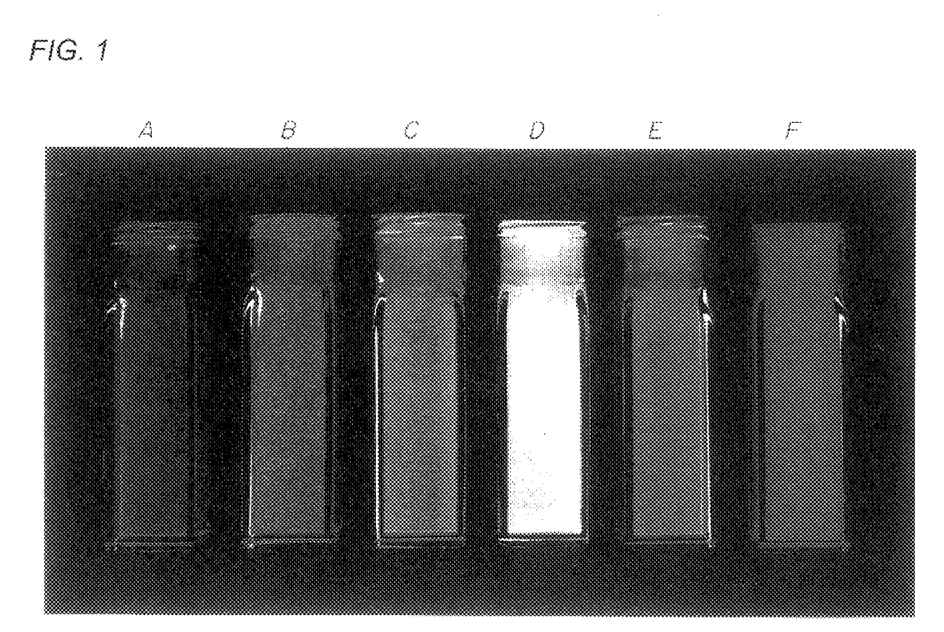
FIG. 1 depicts a color photograph of several suspensions of different sizes of ZnS overcoated CdSe quantumdots in hexane, illustrating the wide range of colors that can be utilized in the present invention.

As discussed above, the selection of the composition of the quantum dot, as well as the size of the quantum dot, affects the characteristic spectral emission wavelength of the quantum dot. Thus, as one of ordinary skill in the art will realize, a particular composition of a quantum dot as listed above will be selected based upon the spectral region being monitored. For example, quantum dots that emit energy in the visible range include, but are not limited to CdS, CdSe, CdTe, ZnSe, ZnTe, GaP, and GaAs. FIG. 1 depicts a color photograph of several suspensions of different sizes of ZnS overcoated CdSe quantum dots in hexane illustrating the wide wide range of colors available for use in the present invention. Quantum dots that emit energy in the near IR range include, but are not limited to, InP, InAs, InSb, PbS, and PbSe. Finally, quantum dots that emit energy in the blue to near-ultraviolet include, but are not limited to ZnS and GaN. For any particular composition selected for the quantum dots to be used in the inventive system, it is possible to tune the emission to a desired wavelength by controlling the size of the particular composition of the quantum dot. In preferred embodiments, 5–20 discrete emissions (five to twenty different size populations or distributions distinguishable from one another) are obtained for any particular composition, although one of ordinary skill in the art will realize that fewer than five emissions and more than twenty emissions could be used depending on the monodispersity of the quantum dot particles. If high information density is required, and thus a greater number of distinct emissions, the nanocrystals are also substantially monodisperse within the broad nanometer range given above (12–150 Å). By monodisperse, as that term is used herein, it means a colloidal system in which the suspended particles have substantially identical size and shape. In preferred embodiments for high information density applications, monodisperse particles deviate less than 10% rms in diameter, and preferably less than 5%. Monodisperse quantum dots have been described in detail in Murray et al. (*J. Am. Chem. Soc.*, 1993, 115, 8706), and in the thesis of Christopher Murray, "Synthesis and Characterization of II–VI Quantum Dots and Their Assembly into 3-D Quantum Dot Superlattices", Massachusetts Institute of Technology, September, 1995, which are hereby incorporated in their entireties by reference. One of ordinary skill in the art will also realize that the number of discrete emissions that can be distinctly observed for a given composition depends not only upon the monodispersity of the particles, but also on the deconvolution techniques employed. Quantum dots, unlike dye molecules, can be easily modeled as Gaussians and therefore are more easily and more accurately deconvoluted.

However, for some applications high information density will not be required and it may be more economically attractive to use more polydisperse particles. Thus, for applications that do not require high information density, the linewidth of the emission may be in the range of 40–60 nm.

In addition to the ability to tune the emission energy by controlling the size of the particular quantum dot, the intensities of that particular emission observed at a specific wavelength are also capable of being varied, thus increasing the potential information density provided by the quantum dot "barcode" system. In preferred embodiments, 2–15 different intensities may be achieved for a particular emission at a desired wavelength, however, one of ordinary skill in the art will realize that more than fifteen different intensities may be achieved, depending upon the particular application of the inventive identification units. For the purposes of the present invention, different intensities may be achieved by varying the concentrations of the particular size quantum dot attached to, embedded within or associated with an item or component of interest.

In a particularly preferred embodiment, the surface of the quantum dot is also modified to enhance the efficiency of the emissions, by adding an overcoating layer to the quantum dot. The overcoating layer is particularly preferred because at the surface of the quantum dot, surface defects can result in traps for electron or holes that degrade the electrical and optical properties of the quantum dot. An insulating layer at the surface of the quantum dot provides an atomically abrupt jump in the chemical potential at the interface which eliminates energy states that can serve as traps for the electrons and holes. This results in higher efficiency in the luminescent process.

Suitable materials for the overcoating layer include semiconductors having a higher band gap energy than the quantum dot. In addition to having a band gap energy greater than the quantum dots, suitable materials for the overcoating layer should have good conduction and valence band offset with respect to the quantum dot. Thus, the conduction band is desirably higher and the valence band is desirably lower than those of the quantum dot. For quantum dots that emit energy in the visible (e.g., CdS, CdSe, CdTe, ZnSe, ZnTe, GaP, GaAs) or near IR (e.g., InP, InAs, InSb, PbS, PbSe), a material that has a band gap energy in the ultraviolet regions may be used. Exemplary materials include ZnS, GaN, and magnesium chalcogenides, e.g., MgS, MgSe, and MgTe. For quantum dots that emit in the near IR, materials having a band gap energy in the visible, such as CdS or CdSe, may also be used. The overcoating layer may include as many as eight monolayers of the semiconductor material. The preparation of a coated quantum dot may be found in U.S. Ser. No. 08/969,302, U.S. Pat. No. 6,322,901 filed Nov. 13, 1997 and entitled "Highly Luminescent Color-Selective Materials", and Dabbousi et al., (*J. Phys. Chem. B,* 1997, 101, 9463) and Kuno et al., (*J. Phys. Chem.,* 1997, 106, 9869).

After selection of a particular collection of quantum dot composition and sizes as discussed above to associate with an item of interest, the quantum dots can be attached to, embedded within or associated with that particular item of interest. As one of ordinary skill in the art will realize, the item of interest must be sufficiently reactive with the surface of the quantum dot, or must be sufficiently compatible with the quantum dot.

Figure 2:
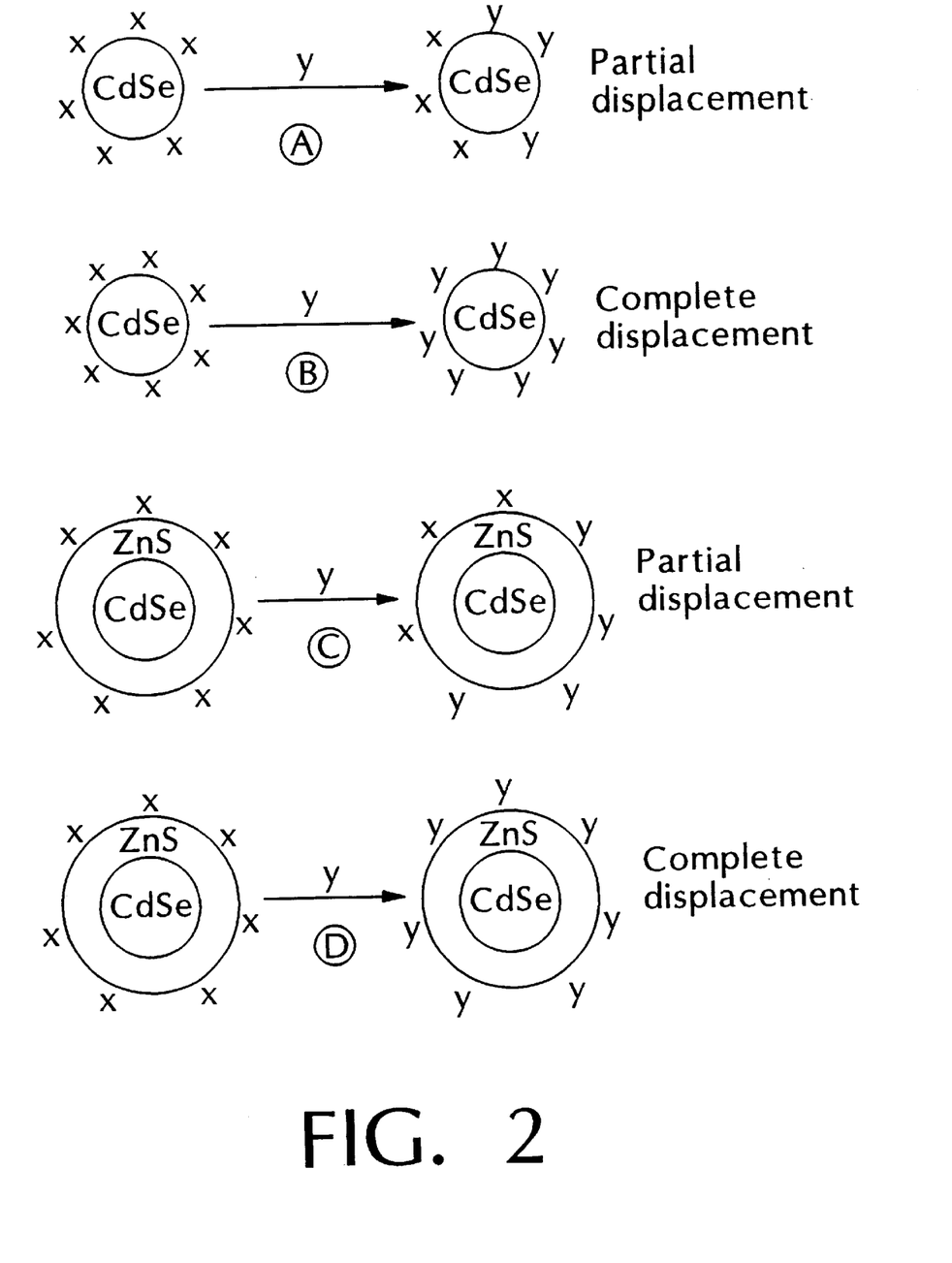
FIG. 2 depicts a general displacement reaction to modify the surface of the quantum dot.

Most quantum dots are prepared in coordinating solvent, such as trioctylphosphine oxide (TOPO) and trioctyl phosphine (TOP) resulting in the formation of a passivating organic layer on the dot surface comprised of the organic solvent. This layer is present on quantum dots containing an overcoating and those that do not contain an overcoating. Thus, either of these classes of passivated quantum dots are readily soluble in organic solvents, such as toluene, chloroform and hexane. As one of ordinary skill in the art will realize, these functional moieties may be readily displaced or modified to provide an outer coating that renders the quantum dots suitable for use as the identification units of the present invention. Furthermore, based upon the desired application, a portion of the quantum dot functionality, or the entire surface of the quantum dot functionality may be modified by a displacement reaction, based upon the desired application of the inventive identification units. FIG. 2 depicts general displacement reactions of certain functional moieties to provide a quantum dots with modified functionalities for use in the inventive method. FIG. 2 also depicts the ability to displace a specific percentage of moieties on the surface of the quantum dots. For example, reaction A, depicts the partial displacement of moiety X by moiety Y, whereas reaction B depicts the complete displacement of moiety X by moiety Y for a quantum dot having no overcoating layer. Reactions C and D depict the partial and complete displacement reactions for overcoated quantum dots, respectively. In general, moieties such as TOPO and TOP, as well as other moieties may be readily displaced and replaced with other functional moieties, including, but not limited to carboxylic acids, amines, aldehydes, and styrene to name a few. One of ordinary skill in the art will realize that factors relevant to the success of a particular displacement reaction include the concentration of the replacement moiety, temperature and reactivity. Thus, for the purposes of the present invention, any functional moiety may be utilized that is capable of displacing an existing functional moiety to provide a quantum dot with a modified functionality for a specific use of the identification units of the present invention.

The ability to utilize a general displacement reaction to selectively modify the surface functionality of the quantum dots enables functionalization for specific uses of the inventive identification units. In one particularly preferred embodiment, water soluble quantum dots are provided for use in aqueous environments. In the case of water-soluble quantum dots, the outer layer includes a compound having at least one linking moiety that attaches to the surface of the particle and that terminates in at least one hydrophilic moiety. The linking and hydrophilic moieties are spanned by a hydrophobic region sufficient to prevent charge transfer across the region. The hydrophobic region also provides a "pseudo-hydrophobic" environment for the nanocrystal and thereby shields it from aqueous surroundings. A detailed description of methods for making water soluble quantum dots may be found in the application entitled "Water Soluble Luminescent Nanocrystals" filed the same day herewith, and incorporated in its entirety by reference. In preferred embodiments, the hydrophilic moiety may be a polar or charged (positive or negative) group. The polarity or charge of the group provides the necessary hydrophilic interactions with water to provide stable solutions or suspensions of the quantum dot. Exemplary hydrophilic groups include polar groups such as hydroxides (—OH), amines, polyethers, such as polyethylene glycol and the like, as well as charged groups, such as carboxylates (—$CO^{2-}$), sulfonates (—$SO^{3-}$), phosphates (—$PO_4^{2-}$ and —$PO_3^{2-}$), nitrates, ammonium salts (—$NH^{4+}$), and the like.

In another particularly preferred embodiment, a displacement reaction may be employed to modify the quantum dot to improve the solubility in a particular organic solvent. For example, if it is desired to associate the quantum dots with a particular solvent or liquid, such as pyridine, the surface can be specifically modified with pyridine or pyridine-like moieties to ensure salvation.

In yet another particularly preferred embodiment, the surface layer is modified by displacement to render the quantum dot reactive for a particular coupling reaction. For example, displacement of TOPO moieties with a group containing a carboxylic acid moiety enables the reaction of the modified quantum dots with amine containing moieties (commonly found on solid support units) to provide an amide linkage.

Likewise, the surface of the quantum dot can also be modified to create a surface on the quantum dot similar to an object that the quantum dot will be associated with. For example, the quantum dot surface can be modified using a displacement reaction to create styrene or acrylate moieties, thus enabling the incorporation of the quantum dots into polystyrene, polyacrylate or other polymers.

After selection of the composition of quantum dot for the desired range of spectral emission and selection of a desired surface functionalization compatible with the system of interest, it may also be desirable to select the minimum number of quantum dots needed to observe a distinct and unique spectral emission of sufficient intensity for spectral identification. Selection criteria important in determining the minimum number of quantum dots needed to observe a distinct and unique spectral emission of sufficient intensity include providing a sufficient number of quantum dots that are bright (i.e., that emit light versus those that are dark) and providing a sufficient number of quantum dots to average out over the blinking effect observed in single quantum dot emissions (Mnirmal et al., Nature, 1996, 383, 802). In one particularly preferred embodiment, at least eight quantum dots of a particular composition and particle size distribution are provided. For example, if a "barcode" were provided that utilized three different particle size distributions of a particular composition, it would be most desirable to utilize eight of each of the three different particle size distributions of a quantum dot, in order to observe sufficiently intense spectral emissions from each to provide reliable information regarding the location or identity of a particular item or matter of interest. One of ordinary skill in the art will realize, however, that fewer than eight quantum dots of a particular composition and particle size distribution could be utilized provided that a unique spectral emission of sufficient intensity is observed, as determined by the selection criteria set forth above.

As discussed previously, the ability of the quantum dots to produce discrete optical transitions, along with the ability to vary the intensity of these optical transitions, enables the development of a versatile and dense encoding scheme. The characteristic emissions produced by one or more sizes of quantum dots attached to, associated with, or embedded within a particular support or matter enables the identification of the item or composition of interest and/or its location. For example, by providing N sizes of quantum dots (each having a discrete optical transition), each having M distinguishable states resulting from the absence of the quantum dot, Qr from different intensities resulting from a particular discrete optical transition, $M^n$ different states can be uniquely defined. In the case of M=2 where the two states could be the presence or absence of the quantum dot, the encoding scheme would thus be defined by a base 2 or binary code. In the case of M=3 where the three states could be the presence of a quantum dot at two distinguishable intensities or its absence, the encoding scheme would be defined by a base 3 code. Herein, such base M codes where M>2 are termed higher order codes. The advantage of higher order codes over a binary order code is that fewer identifiers are required to encode the same quantity of information.

As one of ordinary skill in the art will realize, the ability to develop a higher order encoding system is dependent upon the number of different intensities capable of detection by both the hardware and the software utilized in the decoding system. In particularly preferred embodiments, each discrete emission or color, is capable of being detectable at two to twenty different intensities. In a particularly preferred embodiment wherein ten different intensities are available, it is possible to employ a base 11 code comprising the absence of the quantum dot, or the detection of the quantum dot at 10 different intensities.

Clearly, the advantages of the quantum dots, namely the ability to observe discrete optical transitions at a plurality of intensities, provides a powerful and dense encoding scheme that can be employed in a variety of disciplines. In general, one or more quantum dots may act as a barcode, wherein each of the one or more quantum dots produces a distinct emissions spectrum. These characteristic emissions can be observed as colors, as shown in FIG. 1, if in the visible region of the spectrum, or may also be decoded to provide information about the particular wavelength at which the discrete transition is observed. Likewise, for quantum dots producing emissions in the infared or ultraviolet regions, the characteristic wavelengths that the discrete optical transitions occur at provide information about the identity of the particular quantum dot, and hence about the identity of or location of the item or matter of interest.

An example of a specific system for automated detection that could be employed for use in the present invention includes, but is not limited to, an imaging scheme comprising an excitation source, a monochromator (or any device capable of spectrally resolving the image, or a set of narrow band filters) and a detector array. In one embodiment, the apparatus would consist of a blue or UV source of light, of a wavelength shorter than that of the luminescence detected. This could be a broadband UV light source, such as a deuterium lamp with a filter in front; the output of a white light source such as a xenon lamp or a deuterium lamp after passing through a monochromator to extract out the desired wavelengths; or any of a number of cw gas lasers including but not limited to any of the Argon Ion laser lines (457, 488, 514, etc. nm), a HeCd laser; solid state diode lasers in the blue such as GaN and GaAs (doubled) based lasers or the doubled or tripled output of YAG or YLF based lasers; or any of the pulsed lasers with output in the blue, to name a few. The luminescence from the dots would be passed through an imaging subtracting double monochromator (or two single monochromators with the second one reversed from the first), for example, consisting of two gratings or prisms and a slit between the two gratings or prisms. The monochromators or gratings or prisms can also be replaced with a computer controlled color filter wheel where each filter is a narrow band filter centered at the wavelength of emission of one of the dots. The monochromator assembly has more flexibility because any color can be chosen as the center wavelength. Furthermore, a CCD camera or some other two dimensional detector records the images, and software color codes that image to the wavelength chosen above. The system then moves the gratings to a new color and repeats the process. As a result of this process, a set of images of the same spatial region is obtained and each is color-coded to a particular wavelength which is needed to rapidly analyze the data.

In another preferred embodiment, the apparatus is a scanning system as opposed to the above imaging scheme. In a scanning scheme, the sample to be analyzed is scanned with respect to a microscope objective. The luminescence is put through a single monochromator or a grating or prism to spectrally resolve the colors. The detector is a diode array that then records the colors that are emitted at a particular spatial position. The software then ultimately recreates the scanned image and decodes it.

More particularly, specific preferred embodiments for uses of the inventive encoding system are described with reference to the following examples. These examples are provided only for the purposes of illustration and are not intended to limit the scope of the present invention.

Applications to Fluid Dynamics and Microfluidics

Figure 3:
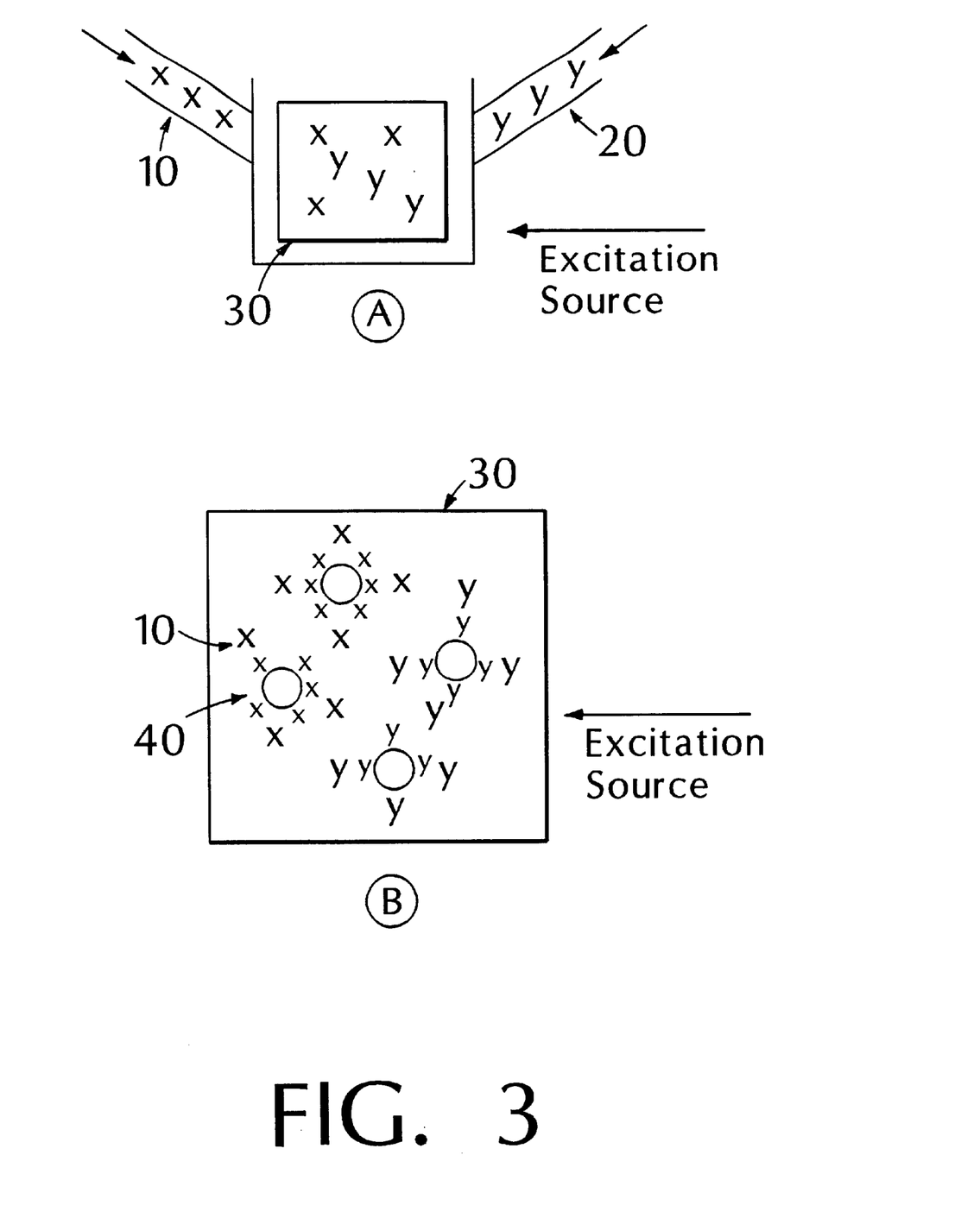
FIG. 3 depicts the use of the inventive system in fluid dynamics.

In one particularly preferred embodiment, the inventive system can be utilized to track or trace the location of a component of interest. For example, fluid dynamics involves generally monitoring the interaction between different fluid components, and thus the location of individual molecules of the desired fluid provides valuable information about the effectiveness of and the degree of interaction between separate components, specifically the controlled movement and mixing of components. In the method of the present invention, one of ordinary skill in the art will realize that the quantum dots can be appropriately functionalized to facilitate interaction with the desired component of interest (so that the quantum dots are compatible with the fluid they are intended to act as tracers for), as discussed in detail earlier, and subsequent mixing of the individual components can be effected. In but one example, if the interaction between two fluids having different characteristics, such as pyridine and dimethylsulfoxide, is being studied, the surface of the quantum dots can be modified with pyridine or dimethylsulfoxide moieties to ensure association of or compatibility of a particular size distribution of quantum dots with the appropriate fluid. Because each the quantum dots are specifically associated with a particular component, it is then possible to take a photograph of the reaction mixture with an ultraviolet lamp and, based upon the discrete optical emissions produced from the quantum dots, gain information about the degree of interaction of the individual components. FIG. 3 depicts a general method for fluid dynamics, wherein two streams of fluid (10) and (20), represented by X and Y in FIG. 3, are introduced into a reaction chamber (30) and the mixing of the fluids is monitored by taking a "picture" at a given time with an excitation source to observe the position of the quantum dots associated with the particular fluid. FIG. 3B depicts an enlargement of the reaction chamber (30) and shows the association of the quantum dots (40) with a particular fluid of interest (10). One of ordinary skill in the art will realize that the ability of the quantum dots to produce discrete transitions enables the mixing of N components, where N represents the number of discrete transitions.

One particularly preferred application for this system for location identification described above is the monitoring of microfluidic molecular systems (MicroFlumes). These microfluidic systems perform multiple reaction and analysis techniques in one microinstrument for specificity and validation, they are completely automated, they contain multiple parallel reaction paths (as opposed to the sequential analysis required today) and provide the capability for hundreds of operations to be performed without manual intervention. (See http:/Hweb-ext2.darpa.mil/eto/mFlumes/index.html)

The semiconductor nanocrystal quantum dots can be used as in the general method described above, where each quantum dot or combination thereof can be associated with or attached to a specific component of interest and upon mixing of the various components, and providing a primary light source, can provide information about the degree and type of interaction between the different components. One of ordinary skill in the art will realize that the inventive encoding system is not limited to the fluid dynamics applications described above; rather the inventive system is capable of being utilized in any system where the tracking of the location of a component or item, such as a gas, liquid, solid, or consumer item (such as dry-cleaned clothing) is desired.

Identification of an Object

Figure 4:
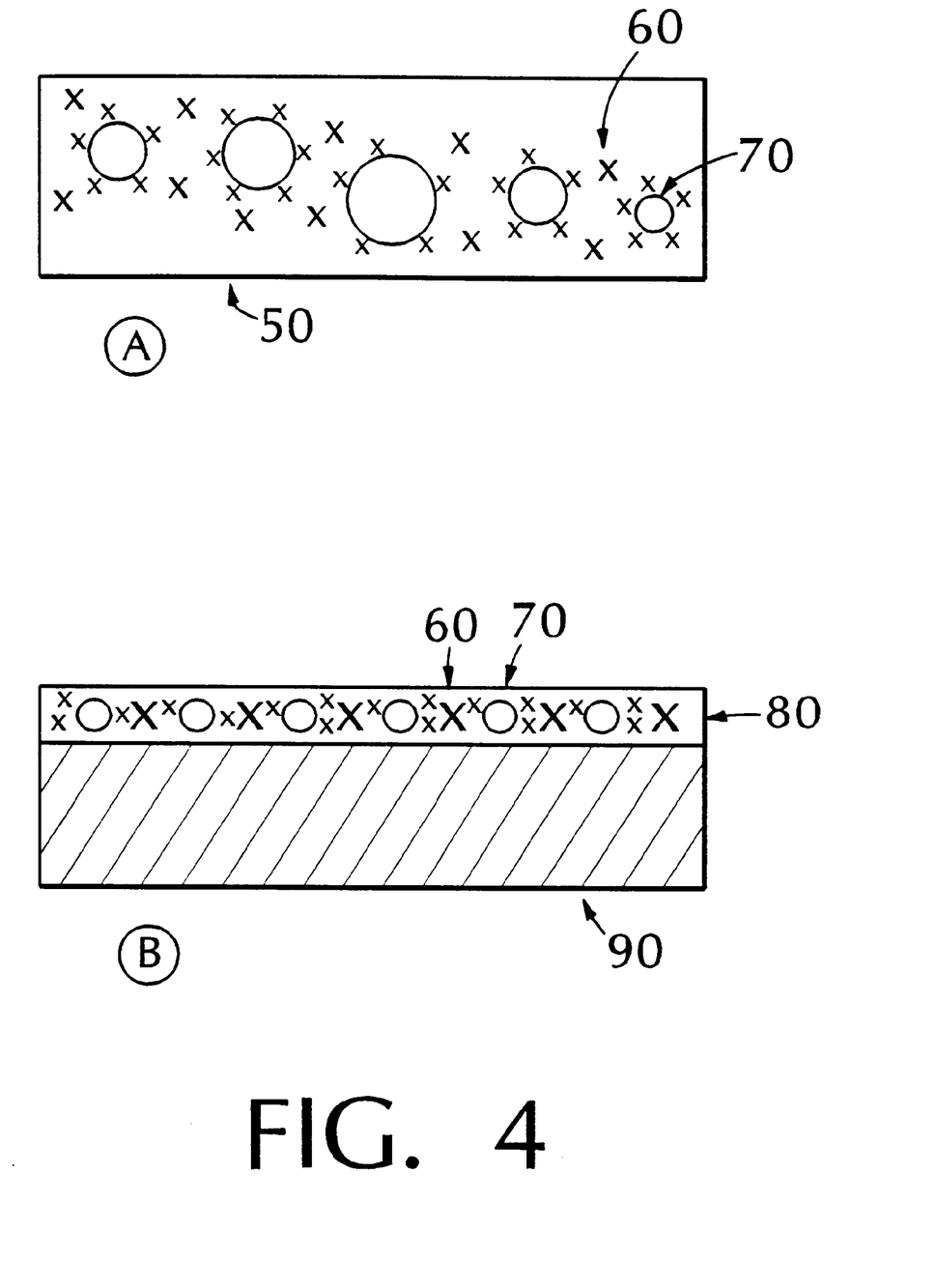
FIG. 4 depicts the use of the inventive system in the identification of an object of interest.

The system of the present invention can also be utilized to identify specific objects including, but not limited to, jewelry, paper, biomolecules such as DNA, vehicles and identification cards. For example, the quantum dots can be appropriately functionalized for incorporation into or attachment to the surface of the object of interest, as discussed above, and as shown in FIG. 4. FIG. 4A depicts the incorporation of the quantum dots into an item of interest (50), wherein the surface of quantum dot has been modified to enable incorporation into the item of interest. FIG. 4B depicts the coating of a quantum dot composition (80) into an item of interest (90), wherein the surface of the quantum dot (70) is modified to interact with the composition medium X (60). In but one example, the quantum dot surface may be functionalized with a specific percentage of amine moieties, thus enabling incorporation into paper, which is comprised of carbohydrate moieties. In other embodiments, the quantum dots may be appropriately functionalized with moieties such as styrene or acrylate to enable incorporation into polymers. The polymers containing the identification units can then be coated onto, or incorporated within specific items such as identification cards. The ease with which the quantum dots can be incorporated into the item and the fact that the quantum dot based "barcode" is invisible, provides a useful system for labeling objects. The ability of the quantum dot "barcode" system to encode large amounts of information, and thus large numbers of items, provides an advantage over existing barcode or microparticle systems discussed previously. The identification of the item of interest from a collection of items can be effected by providing a primary light source and correlating the spectral emissions to a collection of quantum dots which encode a particular item of interest. In another particularly preferred embodiment, the present system may be utilized to keep track of the identity of biomolecules, such as DNA sequences, while they are subjected to reaction processes and chemical manipulations. The biomolecules, or DNA sequences, could be "tagged" themselves, or, alternatively, the biomolecules could be attached to a support, wherein the support is "tagged" with one or more sizes of quantum dots encoding the identity of the DNA sequence.

Encoding Combinatorial Libraries

In another particularly preferred embodiment, the inventive quantum dots may also be used to identify a particular compound in a library of compounds by encoding a particular reaction sequence employed for each of the compounds in the synthesis of complex combinatorial libraries, and thus acting as an identifier. Because of the desirability for the production of large numbers of complex compounds, particularly using a split and pool method, the development of encoding techniques to identify each compound of interest has become important. Because of the small quantity of final product or compound produced from such methods, identifying these products would generally not be feasible. However, by associating each stage or combination of stages of the serial synthesis with an identifier which defines the choice of variables such as reactant, reagent, reaction conditions, or a combination of these, one can use the identifiers to define the reaction history of each definable and separable substrate. The spectral analysis of the quantum dots allows for ready identification of the reaction history. For example, one can determine a characteristic of a product of a synthesis, usually a chemical or biological characteristic by various screening techniques, and then identify the reaction history and thereby the structure of that product, which has the desired characteristic, by virtue of the quantum dot "barcode" associated with the product.

The use of the instant multiple identification system avoids the necessity of carrying out a complicated cosynthesis which reduces yields and requires multiple protecting groups, and avoids the necessity of using sequenceable tags which are necessarily chemically labile. Both the necessity of multiple protecting groups and the intrinsic instability of all known sequenceable tagging molecules (i.e. nucleic acid or peptide oligomers) severely limit the chemistry which may be used in the synthesis of the library element or ligand. Additionally, the present system avoids the need to cleave the tags from the solid support for analysis.

Moreover, the advantage of providing a distinct and non-overlapping resonance, capable of detection at different intensities, enables the use of a binary encoding system or higher. For example, the absence or presence of a particular size quantum dot could be used in a binary system. However, the use of different intensities, of the same color enables the use of a higher order encoding system, each color intensity encoding a particular characteristic.

According to the method of the present invention, the products to be encoded include, but are not limited to biomolecules (such as peptides and oligonucleotides, organic compounds, and inorganic compounds) and catalysts resulting from combinatorial synthesis. Exemplary combinatorial libraries that can be synthesized using the present encoding method include, but are not limited to peptide libraries, peptidomimetics, carbohydrates, organometallic catalysts and small molecule libraries (For examples see, Kahne, D. *Curr. Opin. Chem. Biol.*, 1997, 1, 130; Hruby et al., *Curr. Opin. Chem. Biol.*, 1997, 1, 114; Gravert et al., *Curr. Opin. Chem. Biol.*, 1997, 1, 107).

In a particularly preferred embodiment, a solid phase synthesis technique such as split and pool synthesis is utilized, in which the desired scaffold structures are attached to the solid phase directly or though a linking unit, as discussed above. Advantages of solid phase techniques include the ability to more easily conduct multi-step reactions and the ability to drive reactions to completion because excess reagents can be utilized and the unreacted reagent washed away. Perhaps one of the most significant advantages of solid phase synthesis is the ability to use a technique called "split and pool", in addition to the parallel synthesis technique, developed by Furka. (Furka et al., *Abstr. 14th Int. Congr. Biochem.*, Prague, Czechoslovakia, 1988, 5,.47; Furka et al., *Int. J. Pept. Protein Res.* 1991,37, 487; Sebestyen et al., *Bioorg. Med Chem. Lett.*, 1993, 3, 413.) In this technique, a mixture of related compounds can be made in the same reaction vessel, thus substantially reducing the number of containers required for the synthesis of very large libraries, such as those containing as many as or more than one million library members. As an example, the solid support scaffolds can be divided into n vessels, where n represents the number species of reagent A to be reacted with the scaffold structures. After reaction, the contents from n vessels are combined and then split into m vessels, where m represents the number of species of reagent B to be reacted with the scaffold structures. This procedure is repeated until the desired number of reagents is reacted with the scaffold structures to yield the inventive library.

The quantum dots of the present invention can be readily attached to a solid support. A solid support, for the purposes of this invention, is defined as an insoluble material to which compounds are attached during a synthesis sequence. The use of a solid support is advantageous for the synthesis of libraries because the isolation of support-bound reaction products can be accomplished simply by washing away reagents from the support-bound material and therefore the reaction can be driven to completion by the use of excess reagents. A solid support can be any material which is an insoluble matrix and can have a rigid or semi-rigid surface. Exemplary solid supports include but are not limited to pellets, disks, capillaries, hollow fibers, needles, pins, solid fibers, cellulose beads, pore-glass beads, silica gels, polystyrene beads optionally cross-linked with divinylbenzene, grafted co-poly beads, poly-acyrlamide beads, latex beads, dimethylacrylamide beads optionally crosslinked with N-N'-bis-acryloylethylenediamine, and glass particles coated with a hydrophobic polyrner. In one particularly preferred embodiment, a Tentagel amino resin, a composite of 1) a polystyrene bead crosslinked with a divinylbenzene and 2) PEG (polyethylene glycol), is employed for use in the present invention. The quantum dots of the present invention can readily be functionalized with styrene and thus can be incorporated into Tentagel beads, or the quantum dots may be functionalized with a carboxylate moiety and can be readily attached to the Tentagel support having an amine moiety through an amide linkage. Tentagel is a particularly useful solid support because it provides a versatile support for use in on-bead or off-bead assays, and it also undergoes excellent swelling in solvents ranging from toluene to water.

Figure 5:
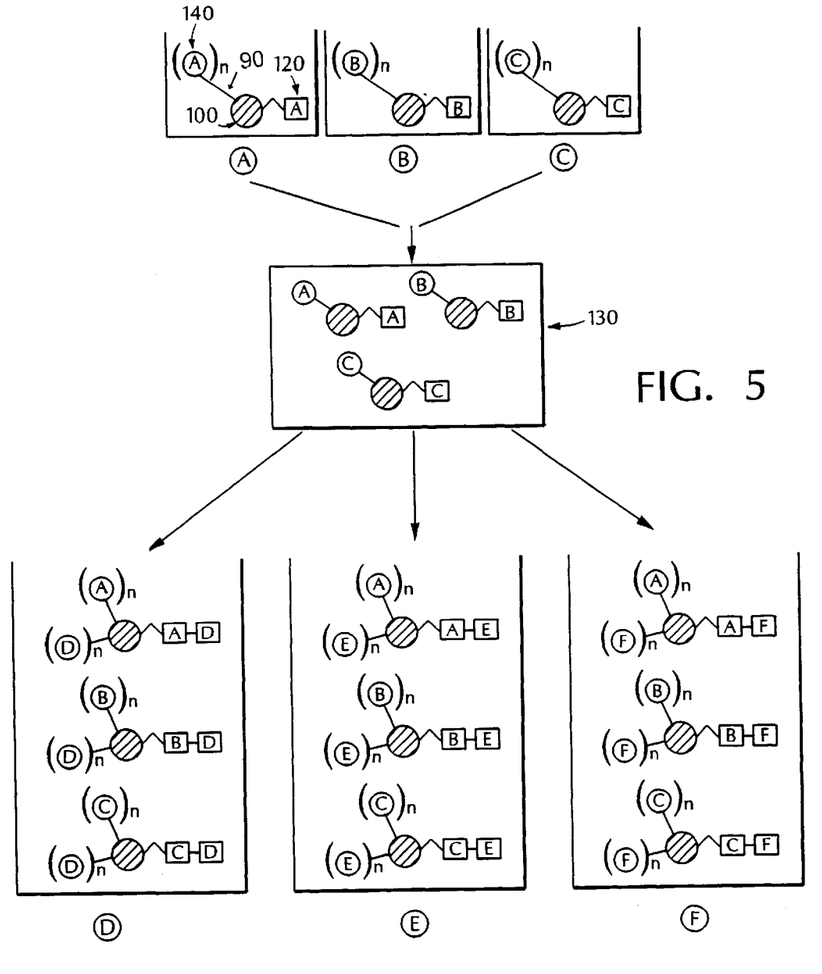
FIG. 5 depicts the use of the inventive system in the encoding of combinatorial libraries.

The quantum dots therefore identify each reaction stage that an individual solid support has experienced, and records the step in the particular synthesis series, as shown in FIG. 5. FIG. 5 depicts the attachment of three different reagents A, B, and C (120) to a solid support, and the attachment of the identification unit (140) to the solid support (100) via a linkage (90). The supports are then pooled together (130) and split for reaction with reagents D, E, and F. Attachment of appropriate identification units for each of these reagents enables the encoding of this particular reaction stage as observed previously for reagents A, B, and C. In this particular embodiment, the tags may be attached to all (or most) of the solid supports immediately before, during, or immediately after the reaction stage, depending on the particular chemistry used in a given reaction sequence.

In another preferred embodiment, the beads can be labeled with the quantum dots prior to reaction of the beads with any reagents, and as the beads are split in the split and pool process, the beads are read before being added to a new (split stage) container to keep track of the particular reaction at that particular stage in the synthesis.

Once the synthesis is complete, the library of compounds can then be screened for biological activity and the supports having a compound of interest can then be analyzed directly (on-bead analysis) to provide information about the reaction stages and history of the synthesis.

Although the method described above is with reference to split and pool combinatorial techniques, one of ordinary skill in the art will realize that the present encoding scheme is not limited to split and pool methods; rather the inventive encoding scheme can be utilized in any combinatorial or other reaction scheme such as parallel synthesis, or synthesis of compounds on an array, to name a few.

Genomics Applications

In another particularly preferred embodiment of the present invention, the inventive system can be utilized to gain information about genetic information from oligonucleotide fragments. In general, it has been desirable to understand genetic variation and its consequences on biological function, and in order to do this, an enormous comparative sequence analysis must be carried out. Because each DNA strand has the capacity to recognize a uniquely complementary sequence through base pairing, the process of recognition, or hybridization, is highly parallel, as every nucleotide in a large sequence can in principle be queried at the same time.

DNA chip technology has been an important tool for genomics applications. Single nucleotide polymorphisms (SNPs) are the most frequently observed class of variations in the human genome. Detecting the differences between alleles of genes is a significant goal of medical research into genetic diseases and disorders. (For example, sickle cell anemia, colon cancer, BRCA1). Current technology has allowed for large scale screening of DNA sequences for mutations in the sequence. This technology involves the creation of DNA "chips" that contain high-density arrays of DNA sequences (e.g. STSs) covalently bound at specific locations on a surface (glass). A set of four oligonucleotides of identical sequence except for a single base alteration (A, G, T, or C) near the center is used to compare two alleles of a gene. Single nucleotide differences between alleles at the position complementary to altered sites in the set of four oligos will allow one oligo to hybridize preferentially over the other three. Detecting which oligo hybridizes to the sample DNA will then identify the sequence of the polymorphism. By creating sets of these four oligos that are shifted over by one nucleotide each, a researcher can scan a large number of basepairs for single nucleotide polymorphisms.

The system of the present invention, in contrast to fluorescently labeled probes used in the existing methods, is capable of not only acting as a probe for identification of a desired sequence, but is also capable of encoding information about the sequence itself. Because the inventive identification system is capable of providing both a probe and identifier, ordered arrays are not necessary for accessing genetic information, although the inventive system can still be used in traditional arrays. Instead, a collection of beads, for example, can be assembled with the desired labeled DNA fragments, wherein said beads are also encoded with information about the particular sequence. Upon binding, the oligo that hybridizes to the sample DNA can be detected by scanning the sample to identify the quantum dot labeled probe, while at the same time the sequence information can then be decoded by analyzing the quantum dot "barcode".

What we claim is:

1. A composition comprising a support and more than one particle size distribution of semiconductor nanocrystal,
   wherein the semiconductor nanocrystal is bound to the support, and
   each particle size distribution of semiconductor nanocrystal has a spectral emission distinguishable from the other particle size distributions of semiconductor nanocrystal bound to the support.

2. The composition of claim 1, wherein the semiconductor nanocrystal further comprises an overcoating at a surface of a semiconductor material of the semiconductor nanocrystal.

3. The composition of claim 1, wherein the semiconductor nanocrystal comprises a II–VI, III–V or IV semiconductor material.

4. The composition of claim 1, wherein the semiconductor material comprises ZnS, ZnSe, ZnTe, CdS, CdSe, CdTe, GaN, GaP, GaAs, BaSb, InP, InAs, InSb, AlS, AlP, AlSb, PbS, PbSe, G, or Si, or ternary mixtures or quaternary mixtures thereof.

5. The composition of claim 1, wherein the semiconductor nanocrystal is water soluble.

6. The composition of claim 1, wherein each distinguishable spectral emission is a wavelength, an intensity, a linewidth, or a combination thereof.

7. A composition comprising a support and more than one particle size distribution of semiconductor nanocrystal,
   wherein the semiconductor nanocrystal is bound to the support,
   each particle size distribution of semiconductor nanocrystal has a spectral emission distinguishable from the other particle size distributions bound to the support,
   the semiconductor nanocrystal comprises a semiconductor and an overcoating at a surface of the semiconductor, and
   each distinguishable spectral emission is a wavelength, an intensity, a linewidth, or a combination thereof.

8. The composition of claim 6, wherein each distinguishable spectral emission is a wavelength.

9. The composition of claim 7, wherein each distinguishable spectral emission is a wavelength.

10. The composition of claim 6, wherein each distinguishable spectral emission is a linewidth.

11. The composition of claim 7, wherein each distinguishable spectral emission is a linewidth.

12. The composition of claim 10, wherein each linewidth is in the range of 12 to 60 nm.

13. The composition of claim 11, wherein each linewidth is in the range of 12 to 60 nm.

14. The composition of claim 12, wherein each linewidth is 12 to 15 nm.

15. The composition of claim 13, wherein each linewidth is 12 to 15 nm.

16. A composition comprising a support and more than one particle size distribution of semiconductor nanocrystal,
    wherein the semiconductor nanocrystal is bound to the support,
    each particle size distribution of semiconductor nanocrystal has a spectral emission distinguishable from the other particle size distributions of semiconductor nanocrystal bound to the support, and
    the support is a solid or a fluid.

17. The composition of claim 16, wherein the support is a solid.

18. The composition of claim 17, wherein the solid is a polymer or a glass.

19. The composition of claim 18, wherein the solid is a polymer.

20. The composition of claim 19, wherein the polymer is:
    cellulose,
    polystyrene,
    polyacrylamnide,
    polyacrylate,
    latex,
    cross-linked dimethylacrylamide,
    a polypeptide, or
    an oligonucleotide.

21. The composition of claim 17, wherein the solid is silica.

* * * * *